US006171827B1

(12) United States Patent
Bulleid et al.

(10) Patent No.: US 6,171,827 B1
(45) Date of Patent: Jan. 9, 2001

(54) PROCOLLAGENS

(75) Inventors: Neil Bulleid, Didsbury; Karl Kadler, Stockport, both of (GB)

(73) Assignee: The Victoria University of Manchester, Manchester (GB)

(*) Notice: Under 35 U.S.C. 154(b), the term of this patent shall be extended for 0 days.

(21) Appl. No.: 09/029,348

(22) PCT Filed: Aug. 30, 1996

(86) PCT No.: PCT/GB96/02122

§ 371 Date: May 7, 1998

§ 102(e) Date: May 7, 1998

(87) PCT Pub. No.: WO97/08311

PCT Pub. Date: Mar. 6, 1997

(30) Foreign Application Priority Data

Aug. 31, 1995 (GB) ............................................ 9517773
Mar. 23, 1996 (GB) ............................................ 9606152
Jun. 14, 1996 (GB) ............................................ 9612476

(51) Int. Cl.[7] ........................ C12N 15/62; C12N 15/63; C12N 1/00; C12N 5/10; C07K 14/78

(52) U.S. Cl. ................ 435/69.7; 435/69.1; 435/320.1; 435/325; 435/252.3; 435/254.11; 536/23.5; 530/356; 530/353

(58) Field of Search ................... 530/356, 353; 536/23.5; 514/12; 424/9.1; 435/69.7, 69.1, 320.1, 325, 254.11, 252.3

(56) References Cited

U.S. PATENT DOCUMENTS

| 4,545,990 | 10/1985 | Le Foyer de Costil et al. ..... 514/557 |
| 5,424,408 | 6/1995 | Reeders et al. ...................... 536/23.5 |

FOREIGN PATENT DOCUMENTS

| 0 465 104 A1 | 1/1992 | (EP) .............................. C07K/15/00 |
| 93/07889 | 4/1993 | (WO) ............................ A61K/37/00 |
| WO 94/16570 | 8/1994 | (WO) . |

OTHER PUBLICATIONS

Yamagata et al. The complete primary structure of type XII collagen shows a chimeric molecule with reiterated fibronectin type III motifs, von Willebrand Factor A motifs, a domain homologous to a noncollagenous region of Type IX collagen and short collag, Oct. 1991.*

Christiano et al. The large non–collagenous domain (NC–1) of Type VII collagen is amino–termianl and chimeric. Homology to the Type III domains of fibronectin and the A domains of von Willebrand factor. Hum. Mol. Genet. 1(7): 475–481, Oct. 1992.*

Biochemistry, vol. 39, No. 29, Jul. 23, 1991, Easton, PA U.S., pp. 7097–7104, XP000215689 KOU Katayama et al.: "Regulation of extracellular matrix production by chemically synthesized subfragments of type I collagen carboxyl propeptide." See the whole document.

Guzman et al, "Addition of Mannose to Both the Amino– and Carboxy–Terminal . . . ," Biochem. and Biophys. Research Comm., vol. 84, No. 3, pp. 691–698 (1978).

Greenspan et al, "High Levels of Expression of Full Length . . . ," The Journal of Biological Chemistry, vol. 264, No. 34, pp. 20683–20687 (1989).

* cited by examiner

Primary Examiner—Karen Cochrane Carlson
Assistant Examiner—Gabriele E. Bugaisky
(74) Attorney, Agent, or Firm—Nixon & Vanderhye P.C.

(57) ABSTRACT

There is disclosed molecules comprising at least a first moiety having the activity of a procollagen C-propeptide and a second moiety selected from any one of the group of an alien collagen α-chain and non-collagen materials, the first moiety being attached to the second moiety. Also disclosed are collagen molecules, fibrils and fibres comprising a non-natural combination of collagen α-chains, DNA encoding same, expression hosts transformed or transfected with same, transgenic animals and methods of producing a non-natural collagen.

19 Claims, 8 Drawing Sheets

```
                      CP
                      CP
               CP                 A                                                1
alpha1(I)      YYRADD...A   NVVRDRDLEV   DTTLKSLSQQ   IENIRSPEGS   RKNPARTCRD
alpha2(I)      FYRADQPRSA   PSLRPKDYEV   DATLKSLNNQ   IETLLTPEGS   RKNPARTCRD
alpha1(III)    YYGDE....P   MDFKINTDEI   MTSLKSVNGQ   IESLISPDGS   RKNPARNCRD
                 ~             ~         #~   ~~###~~ #  ## ~ ~#~##  ###### ###

2                          3          4  F          5
alpha1(I)      LKMCHSDWKS   GEYWIDPNQG   CNLDAIKVFC   NMETGETCVY   PTQPSVAQKN
alpha2(I)      LRLSHPEWSS   GYYWIDPNQG   CTMEAIKVYC   DFPTGETCIR   AQPENIPAKN
alpha1(III)    LKFCHPELKS   GEYWVDPNQG   CKLDAIKVFC   NMETGETCIS   ANPLNVPRKH
               #~   #~~  #  # ##~#####  # ~~####~#   ~  #####~    ~    ~~~ #~

B             C
alpha1(I)      WYISKNPKDK   RHVWFGESMT   DGFQFEYGGQ   GSDPADVAIQ   LTFLRLMSTE
alpha2(I)      WYRS..SKDK   KHVWLGETIN   AGSQFEYNVE   GVTSKEMATQ   LAFMRLLANY
alpha1(III)    WW.TDSSAEK   KHVWFGESMD   GGFQFSYGNP   ELPEDVLDVQ   LAFLRLLSSR
               #~  ~   ~  ~# ~###~##~~   # ## #                  ~   # #~#~#~##~~

G         6
alpha1(I)      ASQNITYHCK   NSVAYMDQQT   GNLKKALLLK   GSNEIEIRAE   GNSRFTYSVT
alpha2(I)      ASQNITYHCK   NSIAYMDEET   GNLKKAVILQ   GSNDVELVAE   GNSRFTYTVL
alpha1(III)    ASQNITYHCK   NSIAYMDQAS   GNVKKALKLM   GSNEGEFKAE   GNSKFTYTVL
               ##########   ##~####~  ~  ##~###~ #    ###~ #~  ##  ###~###~#

7                                                               8
alpha1(I)      VDGCTSHTGA   WGKTVIEYKT   TKTSRLPIID   VAPLDVGAPD   QEFGFDVGPV   CFL
alpha2(I)      VDGCSKKTNE   WGKTIIEYKT   NKPSRLPFLD   IAPLDIGGAD   HEFFVDIGPV   CFK
alpha1(III)    EDGCTKHTGE   WSKTVFEYRT   RKAVRLPIVD   IAPYDIGGPD   QEFGVDVGPV   CFL
               ###~   #   #~##~~##~#  #  ###~~#  ~## #~#~~#  ~##  #~### ##
```

FIG. 2

| | | |
|---|---|---|
| alpha 1(I) | GGQGSDPADV | AIQLTFLRLM STE |
| alpha 2(I) | NVEGVTSKEM | ATQLAFMRLL ANY |
| alpha 1(II) | GDDNLAPNTA | NVQMTFLRLL STE |
| alpha 1(III) | GNPELPEDVL | DVQLAFLRLL SSR |
| alpha 1(V) | VDAEGNPVGV | .VQMTFLRLL SAS |
| alpha 2(V) | GDHQSPNTAI | .TQMTFLRLL SKE |
| alpha 1(XI) | LDVEGNSINM | .VQMTFLKLL TAS |
| alpha 2(XI) | VDSEGSPVGV | .VQLTFLRLL SVS |

FIG. 3

| Lane | dipyridyl present | procollagen translated |
|---|---|---|
| 2 | No | proα2(I):(III)CP |
| 3 | Yes | proα2(I):(III)CP |
| 4 | No | BGR |
| 5 | Yes | BGR |
| 6 | No | proα1(III):(I)CP |
| 7 | Yes | proα1(III):(I)CP |

Lane 1:- molecular weight markers

| lane | procollagen construct |
|---|---|
| 2 | BGR$^{S-C}$ |
| 3 | BGR |
| 4 | BGR$^{L-M}$ |

Lane 1: molecular weight markers

SEQUENCE LISTING

<160> NUMBER OF SEQ ID NOS: 20

<210> SEQ ID NO 1
<211> LENGTH: 535
<212> TYPE: PRT
<213> ORGANISM: Artificial Sequence
<220> FEATURE:

<223> OTHER INFORMATION: Description of Artificial Sequence: SEQUENCE
      DERIVED FROM cDNA OF PROCOLLAGENS

<400> SEQUENCE: 1

```
Met Leu Ser Phe Val Asp Thr Arg Thr Leu Leu Leu Ala Val Thr
 1               5                  10                  15

Leu Cys Leu Ala Thr Cys Gln Ser Leu Gln Glu Glu Thr Val Arg Lys
             20                  25                  30

Gly Pro Ala Gly Asp Arg Gly Pro Arg Gly Glu Arg Gly Pro Pro Gly
             35                  40                  45

Pro Pro Gly Arg Asp Gly Glu Asp Gly Pro Thr Gly Pro Pro Gly Pro
     50                  55                  60

Pro Gly Pro Pro Gly Pro Pro Gly Leu Gly Gly Asn Phe Ala Ala Gln
 65                  70                  75                  80

Tyr Asp Gly Lys Gly Val Gly Leu Gly Pro Gly Pro Met Gly Leu Met
                 85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
            115                 120                 125

Ala Gly Ala Pro Gly Pro His Gly Pro Val Gly Pro Ala Gly Lys His
            130                 135                 140

Gly Asn Arg Gly Glu Thr Gly Pro Ser Gly Pro Val Gly Pro Ala Gly
145                 150                 155                 160

Ala Val Gly Pro Arg Gly Pro Ser Gly Pro Gln Gly Ile Arg Gly Asp
                165                 170                 175

Lys Gly Glu Pro Gly Glu Lys Gly Pro Arg Gly Leu Pro Gly Phe Lys
            180                 185                 190

Gly His Asn Gly Leu Gln Gly Leu Pro Gly Ile Ala Gly His His Gly
            195                 200                 205

Asp Gln Gly Ala Pro Gly Ser Val Gly Pro Ala Gly Pro Arg Gly Pro
            210                 215                 220

Ala Gly Pro Ser Gly Pro Ala Gly Lys Asp Gly Arg Thr Gly His Pro
225                 230                 235                 240

Gly Thr Val Gly Pro Ala Gly Ile Arg Gly Pro Gln Gly His Gln Gly
                245                 250                 255

Pro Ala Gly Pro Pro Gly Pro Pro Gly Pro Pro Gly Pro Pro Gly Val
            260                 265                 270

Ser Gly Gly Gly Tyr Asp Phe Gly Tyr Asp Gly Asp Phe Tyr Arg Ala
            275                 280                 285

Asp Gln Pro Arg Ser Ala Pro Ser Leu Arg Pro Lys Asp Tyr Glu Val
            290                 295                 300

Asp Ala Thr Leu Lys Ser Leu Asn Asn Gln Ile Glu Thr Leu Leu Thr
305                 310                 315                 320

Pro Glu Gly Ser Arg Lys Asn Pro Ala Arg Thr Cys Arg Asp Leu Arg
                325                 330                 335

Leu Ser His Pro Glu Trp Ser Ser Gly Tyr Tyr Trp Ile Asp Pro Asn
            340                 345                 350

Gln Gly Cys Thr Met Glu Ala Ile Lys Val Tyr Cys Asp Phe Pro Thr
            355                 360                 365

Gly Glu Thr Cys Ile Arg Ala Gln Pro Glu Asn Ile Pro Ala Lys Asn
            370                 375                 380

Trp Tyr Arg Ser Ser Lys Asp Lys Lys His Val Trp Leu Gly Glu Thr
385                 390                 395                 400
```

```
Ile Asn Ala Gly Ser Gln Phe Glu Tyr Asn Val Glu Gly Val Thr Ser
                405                 410                 415

Lys Glu Met Ala Thr Gln Leu Ala Phe Met Arg Leu Leu Ala Asn Tyr
            420                 425                 430

Ala Ser Gln Asn Ile Thr Tyr His Cys Lys Asn Ser Ile Ala Tyr Met
            435                 440                 445

Asp Glu Glu Thr Gly Asn Leu Lys Lys Ala Val Ile Leu Gln Gly Ser
        450                 455                 460

Asn Asp Val Glu Leu Val Ala Glu Gly Asn Ser Arg Phe Thr Tyr Thr
465                 470                 475                 480

Val Leu Val Asp Gly Cys Ser Lys Lys Thr Asn Glu Trp Gly Lys Thr
                485                 490                 495

Ile Ile Glu Tyr Lys Thr Asn Lys Pro Ser Arg Leu Pro Phe Leu Asp
                500                 505                 510

Ile Ala Pro Leu Asp Ile Gly Gly Ala Asp His Glu Phe Phe Val Asp
            515                 520                 525

Ile Gly Pro Val Cys Phe Lys
            530             535

<210> SEQ ID NO 2
<211> LENGTH: 626
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 2

Met Met Ser Phe Val Gln Lys Gly Ser Trp Leu Leu Ala Leu Leu
  1               5                  10                  15

His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
 65                  70                  75                  80

Phe Gly Glu Cys Cys Ala Val Cys Pro Gln Pro Thr Ala Pro Thr
                 85                  90                  95

Arg Pro Pro Asn Gly Gln Gly Pro Gln Gly Pro Lys Gly Asp Pro Gly
                100                 105                 110

Pro Pro Gly Ile Pro Gly Arg Asn Gly Asp Pro Gly Ile Pro Gly Gln
            115                 120                 125

Pro Gly Ser Pro Gly Ser Pro Gly Pro Pro Gly Ile Cys Glu Ser Cys
        130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220
```

```
Gly Pro Ala Gly Lys Asp Gly Glu Ser Gly Arg Pro Gly Arg Pro Gly
225                 230                 235                 240

Glu Arg Gly Leu Pro Gly Pro Gly Ile Lys Gly Pro Ala Gly Ile
            245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
            275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Asn Arg Gly Glu Arg Gly Ser Glu Gly
                325                 330                 335

Ser Pro Gly His Pro Gly Gln Pro Gly Pro Pro Gly Pro Pro Gly Ala
            340                 345                 350

Pro Gly Pro Cys Cys Gly Gly Val Gly Ala Ala Ala Ile Ala Gly Ile
            355                 360                 365

Gly Gly Glu Lys Ala Gly Gly Phe Ala Pro Tyr Tyr Gly Asp Glu Pro
    370                 375                 380

Met Asp Phe Lys Ile Asn Thr Asp Glu Ile Met Thr Ser Leu Lys Ser
385                 390                 395                 400

Val Asn Gly Gln Ile Glu Ser Leu Ile Ser Pro Asp Gly Ser Arg Lys
                405                 410                 415

Asn Pro Ala Arg Asn Cys Arg Asp Leu Lys Phe Cys His Pro Glu Leu
            420                 425                 430

Lys Ser Gly Glu Tyr Trp Val Asp Pro Asn Gln Gly Cys Lys Leu Asp
            435                 440                 445

Ala Ile Lys Val Phe Cys Asn Met Glu Thr Gly Glu Thr Cys Ile Ser
    450                 455                 460

Ala Asn Pro Leu Asn Val Pro Arg Lys His Trp Trp Thr Asp Ser Ser
465                 470                 475                 480

Ala Glu Lys Lys His Val Trp Phe Gly Glu Ser Met Asp Gly Gly Phe
                485                 490                 495

Gln Phe Ser Tyr Gly Asn Pro Glu Leu Pro Glu Asp Val Leu Asp Val
            500                 505                 510

Gln Leu Ala Phe Leu Arg Leu Leu Ser Ser Arg Ala Ser Gln Asn Ile
            515                 520                 525

Thr Tyr His Cys Lys Asn Ser Ile Ala Tyr Met Asp Gln Ala Ser Gly
    530                 535                 540

Asn Val Lys Lys Ala Leu Lys Leu Met Gly Ser Asn Glu Gly Glu Phe
545                 550                 555                 560

Lys Ala Glu Gly Asn Ser Lys Phe Thr Tyr Thr Val Leu Glu Asp Gly
                565                 570                 575

Cys Thr Lys His Thr Gly Glu Trp Ser Lys Thr Val Phe Glu Tyr Arg
            580                 585                 590

Thr Arg Lys Ala Val Arg Leu Pro Ile Val Asp Ile Ala Pro Tyr Asp
    595                 600                 605

Ile Gly Gly Pro Asp Gln Glu Phe Gly Val Asp Val Gly Pro Val Cys
    610                 615                 620

Phe Leu
625
```

-continued

```
<210> SEQ ID NO 3
<211> LENGTH: 623
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 3

Met Met Ser Phe Val Gln Lys Gly Ser Trp Leu Leu Leu Ala Leu Leu
 1               5                  10                  15

His Pro Thr Ile Ile Leu Ala Gln Gln Glu Ala Val Glu Gly Gly Cys
             20                  25                  30

Ser His Leu Gly Gln Ser Tyr Ala Asp Arg Asp Val Trp Lys Pro Glu
         35                  40                  45

Pro Cys Gln Ile Cys Val Cys Asp Ser Gly Ser Val Leu Cys Asp Asp
     50                  55                  60

Ile Ile Cys Asp Asp Gln Glu Leu Asp Cys Pro Asn Pro Glu Ile Pro
 65                  70                  75                  80

Phe Gly Glu Cys Cys Ala Val Cys Pro Gln Pro Pro Thr Ala Pro Thr
                 85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Asn Arg Gly Glu Arg Gly Ser Glu Gly
                325                 330                 335

Ser Pro Gly His Pro Gly Gln Pro Gly Pro Pro Gly Pro Pro Gly Ala
            340                 345                 350

Pro Gly Pro Cys Cys Gly Gly Val Gly Ala Ala Ala Ile Ala Gly Ile
        355                 360                 365
```

```
Gly Gly Glu Lys Ala Gly Gly Phe Ala Asp Gln Arg Ser Ala Pro Ser
    370                 375                 380

Leu Arg Pro Lys Asp Tyr Glu Val Asp Ala Thr Leu Lys Ser Leu Asn
385                 390                 395                 400

Asn Gln Ile Glu Thr Leu Leu Thr Pro Glu Gly Ser Arg Lys Asn Pro
                405                 410                 415

Ala Arg Thr Cys Arg Asp Leu Arg Leu Ser His Pro Glu Trp Ser Ser
            420                 425                 430

Gly Tyr Tyr Trp Ile Asp Pro Asn Gln Gly Cys Thr Met Glu Ala Ile
        435                 440                 445

Lys Val Tyr Cys Asp Phe Pro Thr Gly Glu Thr Cys Ile Arg Ala Gln
    450                 455                 460

Pro Glu Asn Ile Pro Ala Lys Asn Trp Tyr Arg Ser Ser Lys Asp Lys
465                 470                 475                 480

Lys His Val Trp Leu Gly Glu Thr Ile Asn Ala Gly Ser Gln Phe Glu
                485                 490                 495

Tyr Asn Val Glu Gly Val Thr Ser Lys Glu Met Ala Thr Gln Leu Ala
            500                 505                 510

Phe Met Arg Leu Leu Ala Asn Tyr Ala Ser Gln Asn Ile Thr Tyr His
        515                 520                 525

Cys Lys Asn Ser Ile Ala Tyr Met Asp Glu Glu Thr Gly Asn Leu Lys
    530                 535                 540

Lys Ala Val Ile Leu Gln Gly Ser Asn Asp Val Glu Leu Val Ala Glu
545                 550                 555                 560

Gly Asn Ser Arg Phe Thr Tyr Thr Val Leu Val Asp Gly Cys Ser Lys
                565                 570                 575

Lys Thr Asn Glu Trp Gly Lys Thr Ile Ile Glu Tyr Lys Thr Asn Lys
            580                 585                 590

Pro Ser Arg Leu Pro Phe Leu Asp Ile Ala Pro Leu Asp Ile Gly Gly
        595                 600                 605

Ala Asp His Glu Phe Phe Val Asp Ile Gly Pro Val Cys Phe Lys
    610                 615                 620

<210> SEQ ID NO 4
<211> LENGTH: 537
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 4

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95
```

-continued

```
Gly Pro Arg Gly Pro Pro Gly Ala Ala Gly Ala Pro Gly Pro Gln Gly
            100                 105                 110
Phe Gln Gly Pro Ala Gly Glu Pro Gly Glu Pro Gly Gln Thr Gly Pro
            115                 120                 125
Ala Gly Ala Pro Gly Pro His Gly Pro Val Gly Pro Ala Gly Lys His
            130                 135                 140
Gly Asn Arg Gly Glu Thr Gly Pro Ser Gly Pro Val Gly Pro Ala Gly
145                 150                 155                 160
Ala Val Gly Pro Arg Gly Pro Ser Gly Pro Gln Gly Ile Arg Gly Asp
                165                 170                 175
Lys Gly Glu Pro Gly Glu Lys Gly Pro Arg Gly Leu Pro Gly Phe Lys
            180                 185                 190
Gly His Asn Gly Leu Gln Gly Leu Pro Gly Ile Ala Gly His His Gly
            195                 200                 205
Asp Gln Gly Ala Pro Gly Ser Val Gly Pro Ala Gly Pro Arg Gly Pro
        210                 215                 220
Ala Gly Pro Ser Gly Pro Ala Gly Lys Asp Gly Arg Thr Gly His Pro
225                 230                 235                 240
Gly Thr Val Gly Pro Ala Gly Ile Arg Gly Pro Gln Gly His Gln Gly
                245                 250                 255
Pro Ala Gly Pro Pro Gly Pro Pro Gly Pro Pro Gly Pro Pro Gly Val
            260                 265                 270
Ser Gly Gly Gly Tyr Asp Phe Gly Tyr Asp Gly Asp Phe Tyr Arg Ala
            275                 280                 285
Pro Tyr Tyr Gly Asp Glu Pro Met Asp Phe Lys Ile Asn Thr Asp Glu
        290                 295                 300
Ile Met Thr Ser Leu Lys Ser Val Asn Gly Gln Ile Glu Ser Leu Ile
305                 310                 315                 320
Ser Pro Asp Gly Ser Arg Lys Asn Pro Ala Arg Asn Cys Arg Asp Leu
                325                 330                 335
Lys Phe Cys His Pro Glu Leu Lys Ser Gly Glu Tyr Trp Val Asp Pro
            340                 345                 350
Asn Gln Gly Cys Lys Leu Asp Ala Ile Lys Val Phe Cys Asn Met Glu
            355                 360                 365
Thr Gly Glu Thr Cys Ile Ser Ala Asn Pro Leu Asn Val Pro Arg Lys
        370                 375                 380
His Trp Trp Thr Asp Ser Ser Ala Glu Lys Lys His Val Trp Phe Gly
385                 390                 395                 400
Glu Ser Met Asp Gly Gly Phe Gln Phe Ser Tyr Gly Asn Pro Glu Leu
                405                 410                 415
Pro Glu Asp Val Leu Asp Val Gln Leu Ala Phe Leu Arg Leu Leu Ser
            420                 425                 430
Ser Arg Ala Ser Gln Asn Ile Thr Tyr His Cys Lys Asn Ser Ile Ala
            435                 440                 445
Tyr Met Asp Gln Ala Ser Gly Asn Val Lys Ala Leu Lys Leu Met
        450                 455                 460
Gly Ser Asn Glu Gly Glu Phe Lys Ala Glu Asn Ser Lys Phe Thr
465                 470                 475                 480
Tyr Thr Val Leu Glu Asp Gly Cys Thr Lys His Thr Gly Glu Trp Ser
                485                 490                 495
Lys Thr Val Phe Glu Tyr Arg Thr Arg Lys Ala Val Arg Leu Pro Ile
            500                 505                 510
```

```
Val Asp Ile Ala Pro Tyr Asp Ile Gly Gly Pro Asp Gln Glu Phe Gly
        515                 520                 525

Val Asp Val Gly Pro Val Cys Phe Leu
        530                 535

<210> SEQ ID NO 5
<211> LENGTH: 534
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 5

Met Leu Ser Phe Val Asp Thr Arg Thr Leu Leu Leu Ala Val Thr
  1               5                  10                  15

Leu Cys Leu Ala Thr Cys Gln Ser Leu Gln Glu Glu Thr Val Arg Lys
                 20                  25                  30

Gly Pro Ala Gly Asp Arg Gly Pro Arg Gly Glu Arg Gly Pro Pro Gly
                 35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
 65                  70                  75                  80

Tyr Asp Gly Lys Gly Val Gly Leu Gly Pro Gly Pro Met Gly Leu Met
                 85                  90                  95

Gly Pro Arg Gly Pro Pro Gly Ala Ala Gly Ala Pro Gly Pro Gln Gly
                100                 105                 110

Phe Gln Gly Pro Ala Gly Glu Pro Gly Glu Pro Gly Gln Thr Gly Pro
                115                 120                 125

Gly Ala Pro Gly Pro His Gly Pro Val Gly Pro Ala Gly Lys His Gly
        130                 135                 140

Asn Arg Gly Glu Thr Gly Pro Ser Gly Pro Val Gly Pro Ala Gly Ala
145                 150                 155                 160

Val Gly Pro Arg Gly Pro Ser Gly Pro Gln Gly Ile Arg Gly Asp Lys
                165                 170                 175

Gly Glu Pro Gly Glu Lys Gly Pro Arg Gly Leu Pro Gly Phe Lys Gly
                180                 185                 190

His Asn Gly Leu Gln Gly Leu Pro Gly Ile Ala Gly His His Gly Asp
                195                 200                 205

Gln Gly Ala Pro Gly Ser Val Gly Pro Ala Gly Pro Arg Gly Pro Ala
        210                 215                 220

Gly Pro Ser Gly Pro Ala Gly Lys Asp Gly Arg Thr Gly His Pro Gly
225                 230                 235                 240

Thr Val Gly Pro Ala Gly Ile Arg Gly Pro Gln Gly His Gln Gly Pro
                245                 250                 255

Ala Gly Pro Pro Gly Pro Pro Gly Pro Leu Gly Pro Leu Gly Val Ser
                260                 265                 270

Gly Gly Gly Tyr Asp Phe Gly Tyr Asp Gly Asp Phe Tyr Arg Ala Asp
                275                 280                 285

Gln Pro Arg Ser Ala Pro Ser Leu Arg Pro Lys Asp Tyr Glu Val Asp
        290                 295                 300

Ala Thr Leu Lys Ser Leu Asn Asn Gln Ile Glu Thr Leu Leu Thr Pro
305                 310                 315                 320

Glu Gly Ser Arg Lys Asn Pro Ala Arg Thr Cys Arg Asp Leu Arg Leu
                325                 330                 335
```

-continued

```
Ser His Pro Glu Trp Ser Ser Gly Tyr Tyr Trp Ile Asp Pro Asn Gln
            340                 345                 350

Gly Cys Thr Met Glu Ala Ile Lys Val Tyr Cys Asp Phe Pro Thr Gly
            355                 360                 365

Glu Thr Cys Ile Arg Ala Gln Pro Glu Asn Ile Pro Ala Lys Asn Trp
            370                 375                 380

Tyr Arg Ser Ser Lys Asp Lys Lys His Val Trp Leu Gly Glu Thr Ile
385                 390                 395                 400

Asn Ala Gly Ser Gln Phe Glu Tyr Gly Asn Pro Glu Leu Pro Glu Asp
                405                 410                 415

Val Leu Asp Val Gln Leu Ala Phe Leu Arg Leu Leu Ser Ser Arg Ala
            420                 425                 430

Ser Gln Asn Ile Thr Tyr His Cys Lys Asn Ser Ile Ala Tyr Met Asp
            435                 440                 445

Glu Glu Thr Gly Asn Leu Lys Lys Ala Val Ile Leu Gln Gly Ser Asn
450                 455                 460

Asp Val Glu Leu Val Ala Glu Gly Asn Ser Arg Phe Thr Tyr Thr Val
465                 470                 475                 480

Leu Val Asp Gly Cys Ser Lys Lys Thr Asn Glu Trp Gly Lys Thr Ile
                485                 490                 495

Ile Glu Tyr Lys Thr Asn Lys Pro Ser Arg Leu Pro Phe Leu Asp Ile
            500                 505                 510

Ala Pro Leu Asp Ile Gly Gly Ala Asp His Glu Phe Phe Val Asp Ile
            515                 520                 525

Gly Pro Val Cys Phe Lys
            530

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 6

Gly Asn Pro Glu Leu Pro Glu Asp Val Leu Asp Val Gln Leu Ala Phe
  1               5                  10                  15

Leu Arg Leu Leu Ser Ser Arg
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 7

Gly Gly Gln Gly Ser Asp Pro Ala Asp Val Ala Ile Gln Leu Thr Phe
  1               5                  10                  15

Leu Arg Leu Met Ser Thr Glu
            20

<210> SEQ ID NO 8
<211> LENGTH: 23
<212> TYPE: PRT
<213> ORGANISM: Artificial Sequence
<220> FEATURE:
```

```
<223> OTHER INFORMATION: Description of Artificial Sequence: SEQUENCE
      DERIVED FROM cDNA OF PROCOLLAGENS

<400> SEQUENCE: 8

Asn Val Glu Gly Val Thr Ser Lys Glu Met Ala Thr Gln Leu Ala Phe
 1               5                  10                  15

Met Arg Leu Leu Ala Asn Tyr
             20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 9

Gly Asp Asp Asn Leu Ala Pro Asn Thr Ala Asn Val Gln Met Thr Phe
 1               5                  10                  15

Leu Arg Leu Leu Ser Thr Glu
             20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 10

Val Asp Ala Glu Gly Asn Pro Val Gly Val Val Gln Met Thr Phe Leu
 1               5                  10                  15

Arg Leu Leu Ser Ala Ser
             20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 11

Gly Asp His Gln Ser Pro Asn Thr Ala Ile Thr Gln Met Thr Phe Leu
 1               5                  10                  15

Arg Leu Leu Ser Lys Glu
             20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 12

Leu Asp Val Glu Gly Asn Ser Ile Asn Met Val Gln Met Thr Phe Leu
 1               5                  10                  15

Lys Leu Leu Thr Ala Ser
             20
```

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 13

Val Asp Ser Glu Gly Ser Pro Val Gly Val Gln Leu Thr Phe Leu
  1               5                  10                  15

Arg Leu Leu Ser Val Ser
             20

<210> SEQ ID NO 14
<211> LENGTH: 250
<212> TYPE: PRT
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 14

Tyr Tyr Arg Ala Asp Asp Ala Asn Val Val Arg Asp Arg Asp Leu Glu
  1               5                  10                  15

Val Asp Thr Thr Leu Lys Ser Leu Ser Gln Gln Ile Glu Asn Ile Arg
             20                  25                  30

Ser Pro Glu Gly Ser Arg Lys Asn Pro Ala Arg Thr Cys Arg Asp Leu
         35                  40                  45

Lys Met Cys His Ser Asp Trp Lys Ser Gly Glu Tyr Trp Ile Asp Pro
     50                  55                  60

Asn Gln Gly Cys Asn Leu Asp Ala Ile Lys Val Phe Cys Asn Met Glu
 65                  70                  75                  80

Thr Gly Glu Thr Cys Val Tyr Pro Thr Gln Pro Ser Val Ala Gln Lys
                 85                  90                  95

Asn Trp Tyr Ile Ser Lys Asn Pro Lys Asp Lys Arg His Val Trp Phe
                100                 105                 110

Gly Glu Ser Met Thr Asp Gly Phe Gln Phe Glu Tyr Gly Gly Gln Gly
            115                 120                 125

Ser Asp Pro Ala Asp Val Ala Ile Gln Leu Thr Phe Leu Arg Leu Met
        130                 135                 140

Ser Thr Glu Ala Ser Gln Asn Ile Thr Tyr His Cys Lys Asn Ser Val
145                 150                 155                 160

Ala Tyr Met Asp Gln Gln Thr Gly Asn Leu Lys Lys Ala Leu Leu Leu
                165                 170                 175

Lys Gly Ser Asn Glu Ile Glu Ile Arg Ala Glu Gly Asn Ser Arg Phe
            180                 185                 190

Thr Tyr Ser Val Thr Val Asp Gly Cys Thr Ser His Thr Gly Ala Trp
        195                 200                 205

Gly Lys Thr Val Ile Glu Tyr Lys Thr Thr Lys Thr Ser Arg Leu Pro
    210                 215                 220

Ile Ile Asp Val Ala Pro Leu Asp Val Gly Ala Pro Asp Gln Glu Phe
225                 230                 235                 240

Gly Phe Asp Val Gly Pro Val Cys Phe Leu
                245                 250

<210> SEQ ID NO 15
<211> LENGTH: 21
<212> TYPE: DNA
```

<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 15
aatggagctc ctggacccat g                                       21

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 16
aggtgctgag cgaggctggt cggcaaaacc gccagctttt tc                 42

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 17
ctgctaggta ccaaatggaa ggattcagct tt                           32

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 18
gaccagcctc gctcagca                                           18

<210> SEQ ID NO 19
<211> LENGTH: 1608
<212> TYPE: DNA
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 19
atgctcagct ttgtggatac gcggactttg ttgctgcttg cagtaacctt atgcctagca     60
acatgccaat ctttacaaga ggaaactgta agaaagggcc cagccggaga tagaggacca    120
cgtggagaaa ggggtccacc aggccccca ggcagagatg tgaagatgg tcccacaggc    180 cctcctggtc cacctggtcc tctggcccc cctggtctcg gtgggaactt tgctgctcag    240
tatgatggaa aaggagttgg acttggccct ggaccaatgg gcttaatggg acctagaggc    300
ccacctggtg cagctggagc cccaggccct caaggtttcc aaggacctgc tggtgagcct    360
ggtgaacctg gtcaaactgg tcctgcaggt gcacctggtc ctcatggccc cgtgggtcct    420
gctggcaaac atggaaaccg tggtgaaact ggtccttctg gtcctgttgg tcctgctggt    480
gctgttggcc caagaggtcc tagtggccca caaggcattc gtggcgataa gggagagccc    540
ggtgaaaagg ggcccagagg tcttcctggc ttcaagggac acaatggatt gcaaggtctg    600

```
cctggtatcg ctggtcacca tgtgatcaa ggtgctcctg gctccgtggg tcctgctggt      660
cctaggggcc ctgctggtcc ttctggccct gctggaaaag atggtcgcac tggacatcct      720
ggtacggttg gacctgctgg cattcgaggc cctcagggtc accaaggccc tgctggcccc      780
cctggtcccc ctggccctcc tggacctcca ggtgtaagcg gtggtggtta tgactttggt      840
tacgatggag acttctacag ggctgaccag cctcgctcag caccttctct cagacccaag      900
gactatgaag ttgatgctac tctgaagtct ctcaacaacc agattgagac ccttcttact      960
cctgaaggct ctagaaagaa cccagctcgc acatgccgtg acttgagact cagccaccca     1020
gagtggagca gcggttacta ctggattgac cccaaccaag gatgcactat ggaagccatc     1080
aaagtatact gtgatttccc taccggcgaa acctgtatcc gggcccaacc tgaaaacatc     1140
ccagccaaga actggtatag gagctccaag gacaagaaac acgtctggct aggagaaact     1200
atcaatgctg gcagccagtt tgaatataat gttgaaggag tgacttccaa ggaaatggct     1260
acccaacttg ccttcatgcg cctgctggcc aactatgcct ctcagaacat cacctaccac     1320
tgcaagaaca gcattgcata catggatgag gagactggca acctgaaaaa ggctgtcatt     1380
ctacagggct ctaatgatgt tgaacttgtt gctgagggca cagcaggtt cacttacact      1440 gttcttgtag atggctgctc taaaaagaca aatgaatggg gaaagacaat cattgaatac     1500
aaaacaaata agccatcacg cctgcccttc cttgatattg caccttttgga catcggtggt     1560 gctgaccatg aattctttgt ggacattggc ccagtctgtt tcaaataa                  1608

<210> SEQ ID NO 20
<211> LENGTH: 1881
<212> TYPE: DNA
<213> ORGANISM: Artificial Sequence
<220> FEATURE:
<223> OTHER INFORMATION: Description of Artificial Sequence: SEQUENCE
      DERIVED FROM cDNA OF PROCOLLAGENS

<400> SEQUENCE: 20
atgatgagct ttgtgcaaaa ggggagctgg ctacttctcg ctctgcttca tcccactatt       60
attttggcac aacaggaagc tgttgaagga ggatgttccc atcttggtca gtcctatgcg      120
gatagagatg tctggaagcc agaaccatgc caaatatgtg tctgtgactc aggatccgtt      180
ctctgcgatg acataatatg tgacgatcaa gaattagact gccccaaccc agaaattcca      240
tttggagaat gttgtgcagt ttgcccacag cctccaactg ctcctactcg ccctcctaat      300
ggtcaaggac ctcaaggccc caagggagat ccaggccctc ctggtattcc tgggagaaat      360
ggtgaccctg gtattccagg acaaccaggg tcccctggtt ctcctggccc cctggaatc       420 tgtgaatcat gccctactgg tcctcagaac tattctcccc agtatgattc atatgatgtc      480
aagtctggag tagcagtagg aggactcgca ggctatcctg accagctggg ccccccaggc      540
cctcccggtc ccctggtac atctggtcat cctggttccc ctggatctcc aggataccaa       600
ggaccccctg gtgaacctgg gcaagctggt ccttcaggcc ctccaggacc tctggtgct      660 ataggtccat ctggtcctgc tggaaaagat ggagaatcag gtagacccgg acgacctgga      720
gagcgaggat tgcctggacc tccaggtatc aaaggtccag ctgggatacc tggattccct      780
ggtatgaaag gacacagagg cttcgatgga cgaaatggag aaaagggtga aacaggtgct      840
cctggattaa aggtgaaaa tggtcttcca ggcgaaaatg gagctcctgg acccatgggt      900
ccaagagggc tcctggtgga gcgaggacgg ccaggcttcc tggggctgc aggtgctcgg      960 ggtaatgacg gtgctcgagg taacagaggt gaaagaggat ctgagggctc cccaggccac     1020
```

-continued

```
ccagggcaac caggccctcc tggacctcct ggtgccctg gtccttgctg tggtggtgtt    1080
ggagccgctg ccattgctgg gattggaggt gaaaaagctg gcggttttgc cccgtattat    1140
ggagatgaac caatggattt caaaatcaac accgatgaga ttatgacttc actcaagtct    1200
gttaatggac aaatagaaag cctcattagt cctgatggtt ctcgtaaaaa ccccgctaga    1260
aactgcagag acctgaaatt ctgccatcct gaactcaaga gtggagaata ctgggttgac    1320
cctaaccaag gatgcaaatt ggatgctatc aaggtattct gtaatatgga aactggggaa    1380
acatgcataa gtgccaatcc tttgaatgtt ccacggaaac actggtggac agattctagt    1440
gctgagaaga aacacgtttg gtttggagag tccatggatg gtggttttca gtttagctac    1500
ggcaatcctg aacttcctga agatgtcctt gatgtgcagc tggcattcct tcgacttctc    1560
tccagccgag cttcccagaa catcacatat cactgcaaaa atagcattgc atacatggat    1620
caggccagtg gaaatgtaaa gaaggccctg aagctgatgg ggtcaaatga aggtgaattc    1680
aaggctgaag gaaatagcaa attcacctac acagttctgg aggatggttg cacgaaacac    1740
actggggaat ggagcaaaac agtctttgaa tatcgaacac gcaaggctgt gagactacct    1800
attgtagata ttgcacccta tgacattggt ggtcctgatc aagaatttgg tgtggacgtt    1860
ggccctgttt gcttttttata a                                              1881
```

PROCOLLAGENS

The present invention concerns novel molecules, in particular novel procollagen molecules, together with collagen molecules, fibrils and fibres comprising a non-natural combination of collagen α-chains, DNA encoding same, expression hosts transformed or transfected with same, transgenic animals and methods of producing a non-natural collagen.

Collagen (also known as processed procollagen molecule and triple helical processed procollagen monomeric molecule) (for general reviews see Kadler. K. 1995, Protein Profile, "Extracellular Matrix 1: fibril-forming coliagens", 2: 491–619, Avad, S. et al., 1994, The Extracellular Matrix Facts Book, Academic Press, London, ISBN 0-12-068910-3 and references therein) is a major structural protein in animals where it occurs in the extracellular matrix (ECM) of connective tissues, mostly in the form of fibrils (also known as polymeric collagen). The collagen fibrils (polymeric collagen) are the major source of mechanical strength of connective tissues, providing a substratum for cell attachment and a scaffold for dynamic molecular interactions. The family of collagens comprises complex multidomain proteins comprising three collagen α-chains wound into a triple helix. At least twenty genetically-distinct collagen types have been described to date and they can be classified into subgroups on the basis of gene homology and function of the encoded protein. Fibril-forming collagens (types I, II, III, V and XI; see Table 1) are synthesized as soluble procollagens (also known as proα chains, procollagen α-chains and monomer chains) and comprises a C-propeptide, a Gly-X-Y repeat containing region (which in the case of monomer chains of fibril-forming collagens comprise an uninterrupted collagen α-chain) and an N-propeptide. The proα chains trimerise to form unprocessed procollagen molecules (also known as monomeric procollagen molecules and trimerised proα chains), assembling into fibrillar structures upon enzymic cleavage of their N- and C-terminal propeptide domains (the N- and C-propeptides) (see FIG. 1).

Although the genes encoding the proα chains are remarkably similar, relatively little is known about the processes which control the folding and trimerization of the proα chains (Dion, A. S. and Myers, J. C., 1987, J. Molec. Biol., 193: 127–143), and only a restricted range of collagens is formed. For example, skin fibroblasts synthesise co-incidentally the six highly homologous proα chains (proα1(I), proα1(III), proα1(V), proα2(I), proα2(V) and proα3(V)). Despite the great number of possible combinations of the six proα chains, only specific combinations of collagen chains occur—these are those resulting in types I, III and V collagen. Type I collagen exists as a heterotrimer and assembles with the stoichiometry of two proα1(I) chains and one proα2(I) chain ([proα1(I)]₂ proα2(I)). Homotrimers of proα2(I) have not been detected and hence the inclusion of this chain in a trimer is dependent upon its association with proα1(I) chains. Type III collagens comprise a homotrimer ([proα1(III)]₃), and the constituent chains do not assemble with either of the Type I collagen proα chains. Type V collagen displays heterogeneity with regard to chain composition, forming both homo-([proα3(V)]₃) and heterotrimers ([proα1(V)]₂ proα2(V) and [proα1(V) proα2(V) proα3(V)]).

The C-propeptide is known to be implicated in the assembly of the monomer chains into trimerised proα chains (unprocessed procollagen) prior to cleavage of the N- and C-propeptides and formation of collagen in fibril-forming proα chains. The assembly of the three monomer chains into trimerised proα chains is initiated by association of the C-propeptides. This association can be divided into two stages: an initial recognition event between the proα chains which determines chain selection and then a registration event which leads to correct alignment and folding of the triple helix. Comparison (FIG. 2) of the amino acid sequences of the C-propeptides of proα1(I), proα2(I) and proα1(III) proα chains, which assemble to form collagen types I and III, demonstrates the striking level of sequence similarity between these proα chains yet, despite the homology, they invariably assemble and fold in a collagen type-specific manner.

It has now been found that the C-propeptides, and more particularly certain sequences within them, are not only necessary but are also sufficient to determine the type-specific assembly of the moieties to which they are attached because of the presence of these certain sequences, the C-propeptides are capable of autonomously directing the assembly of the attached moieties, which in particular may be an alien collagen α-chain. The present inventors have isolated and characterised a region of the C-propeptide which defines the chain selection event but which does not affect the subsequent folding. This has allowed the synthesis of novel proα chains which have formed novel trimerised proα chains and collagen. Now that the chain selection interactions between the proα chains can be controlled, a vast range of novel trimeric molecules, in particular collagens, may be synthesised at will using existing and novel proα chains and C-propeptides. These new molecules may possess selected biological and physical properties and have a wide range of uses. For example, novel collagens may be used in industries which use collagen either as a product or as part of a process. Such collagens and uses may include for example: novel gelatins for use in food, food processing and photography; novel finings for clearing yeast during the brewing process, novel gelatins for the food packaging industry; novel polymers for the manufacture of textiles; novel glues for use in construction, building and manufacturing; novel coatings for tablets; novel glues for use with the human or animal body: novel collagens for use as body implants; novel collagens and procollagens as adjuvants; novel collagens and procollagens as molecular carriers for drugs and pharmaceuticals; and as modulators of collagen fibril formation for use in, for example, wound healing and fibrosis.

According to the present invention there is provided a molecule comprising at least a first moiety having the activity of a procollagen C-propeptide and a second moiety selected from any one of the group of an alien collagen α-chain and non-collagen materials, the first moiety being attached to the second moiety.

The molecule may be able to bind to other similar molecules. It may trimerise with other similar molecules.

The first moiety will generally be attached to the C-terminal end of the second moiety, although intervening amino acid residues may be present.

The first moiety may comprise a proα chain C-propeptide or a partially modified form thereof or an analogue thereof, and when forming the C-terminal region of a proα chain, may allow the molecule to bind to other similar molecules. The C-propeptide region of a proα chain may be the C-terminal fragment resulting from C-proteinase cleavage of a proα chain. The C-proteinase may cleave between the residues G and D or A and D or an analogue thereof in the sequence FAPYYGD (residues 376–382 of SEQ ID NO: 2), YYRAD (residues 1–5 of SEQ ID NO: 14) or FYRAD (residues 284–288 of SEQ ID NO: 1) (FIG. 2) or an analogue thereof.

Modifications to molecules may include the addition, deletion or substitution of residues. Substitutions may be conservative substitutions. Modified molecules may have substantially the same properties and characteristics as the molecules form which they are derived. Modified molecules may be homologues of the molecules from which they are derived. They may for example have at least 40% homology, for example 50%, 60%, 70%, 80%, 90% or 95% homology.

The present inventors have isolated and identified (see "Experimental" section) a site—the recognition site—in the procollagen C-propeptide which contains a sequence which is necessary and sufficient to determine the type-specific assembly of the moieties to which it is attached. The recognition site is defined as being the part of the C-propeptide containing the sequence (the recognition sequence) which, in an alignment plot of the C-propeptide against other C-propeptides, corresponds to the sequence in the region between the junction points B and G (FIG. 2). Alignment plots may be done using the PILE-UP program on SEQNET at the Daresbury Laboratories, UK. An existing proα chain which has been substituted at the recognition sequence and as a result has different properties or characteristics is considered to be a molecule comprising a proα chain C-propeptide and an alien collagen α-chain since the C-propeptide is novel, all collagen α-chains therefore being alien to it.

As can be seen from FIG. 2, the recognition sequences contain a region of homologous amino acids. Substitution to the conserved residues (see "Experimental" section below) has not disrupted chain selection nor has it prevented the formation of a correctly aligned helix, and so it appears that the conserved residues are not involved in chain selection. Hence the recognition sequence, although comprising a continuous sequence of about 23 amino acids, may be considered to have the chain selection properties contained within a discontinuous variable sequence. For example in the recognition sequence of alpha 1(III) (SEQ ID NO: 6) the discontinuous variable sequence may be considered to comprise residues 1–12 and 21–23.

The C-propeptide and/or the recognition sequence may be that of a fibrillar proα chain. More generally, the C-propeptide may be an existing C-propeptide, for example a C-propeptide found in nature, or it may be a partially modified form of or an analogue (i.e. possessing substantially the same properties and characteristics but having a different sequence) of an existing proα chain C-propeptide, or it may comprise a novel C-propeptide (i.e. a C-propeptide having significantly different properties or characteristics to other C-propeptides) and may for example have different binding kinetics or α-chain selection properties.

The existing C-propeptide may be selected from any one of the group of the proα1(I), proα2(I), proα1(II), proα1(III), proα1(V), proα2(V), proα3(V), proα1(XI), proα2(XI), and proα3(XI) proα chain C-propeptides or a partially modified form thereof or an analogue thereof. Partially modified forms of procollagen C-propeptides include the recognition sequences of C-propeptides, for example those identified in FIG. 3 of the accompanying drawings in relation to the C-propeptides from which they are derived. In some embodiments of the invention, such modified forms may be the only, or substantially the only, elements derived from a C-propeptide, in other words, no other C-propeptide-derived sequences need be present. However, this will not always be the case, as the invention also encompasses the presence of other parts of the C-propeptide including, of course, the balance of it.

The C-propeptide may comprise an existing C-propeptide or a partially modified form thereof or an analogue thereof substituted at the recognition site. The C-propeptide may be substituted at the recognition site with the recognition sequence of an existing C-propeptide, for example that of a different C-propeptide. It may for example be substituted at the recognition site with the recognition sequence of the C-propeptide of any one of the group of proα1(III), proα1(I), proα2(I), proα1(II), proα1(V), proα2(V), proα1(XI), proα2(XI) and proα3(XI) proα chains. It may be substituted at the recognition site with a recognition sequence having the sequence of any one of the group of SEQ ID NOS: 6–13. The recognition sequence of a C-propeptide which has been modified for example by addition, deletion or substitution of amino acid residues yet which has substantially the same properties and/or characteristics is considered to be essentially that of an existing C-propeptide. The recognition sequence may generally be at least 40% homologous, or even at least 50, 60, 70, 80, 90 or 95% homologous to the sequence from which it was derived.

Such a substitution at the recognition site may significantly affect the properties or characteristics of the C-propeptide.

Alternatively, the recognition sequence may be novel. Such a novel recognition sequence may for example give the first moiety novel binding kinetics or specificity for a novel first moiety or a novel set of first moieties.

The second moiety is a molecular component which may be anything bound to the first moiety. This may include, for example, alien collagen α-chain molecules, or other proteins or fragments of proteins, such as antibodies or antigen binding fragments thereof, or combinations thereof. Proteins constituting or contributing to the second moiety may be glycosylated or otherwise post-translationally modified. By "alien collagen α-chain" is meant a collagen α-chain which does not form part of a proα chain with the C-propeptide in nature; collagen α-chains comprise a triple helical forming domain, and an N-propeptide may also be present. Other collagen α-chains from the same species, as well as those from different species, may be used. Included as collagen α-chains which do not form part of a proα chain with the C-propeptide in nature are partially modified forms and analogues of existing collagen α-chains which form part of a proα chain with the C-propeptide in nature and which do not significantly affect the relevant properties or characteristics of the procollagen molecule, such as binding specificity. Partially modified forms and analogues of collagen α-chains may, for example, have additions, deletions or substitutions which do not significantly affect the relevant properties or characteristics of the C-propeptide or collagen α-chain.

By means of the invention, therefore, novel collagens may be produced. Such novel collagens have combinations of α-chains which are not seen in nature because of the assembly-directing effect of the natural C-propeptides. The invention allows the protein engineer to construct novel collagens having a non-natural combination of α-chains. The invention therefore extends to a procollagen molecule comprising a non-natural combination of α-chains. Non-natural pro-collagen homotrimers and heterotrimers, including all the possible trimers not mentioned in Table 1, are within the scope of the invention.

The second moiety may comprise at least a collagen α-chain. A collagen α-chain may be selected from any one of the group of proα1(I) chain, proα2(I) chain, proα1(II) chain, proα1(III) chain, proα1(V) chain, proα2(V) chain, proα3(V) chain, proα (XI) chain, proα2(XI) chain, and proα3(XI) chain collagen α-chains.

The second moiety may also comprise a proα chain N-propeptide. An N-propeptide may be selected from any one of the group of the proα1(I), proα2(I), proα1(II), proα1(III), proα1(V), proα2(V), proα3(V), proα1(XI), proα2(XI), and proα3(XI) proαchain N-propeptides.

The second moiety may comprise a collagen Δ-chain and N-propeptide which are naturally associated (for example those of the proα2(I) chain), or it may comprise a non-natural combination of collagen α-chain and N-propeptide. Depending upon the host organism in which it may be desired to express molecules of the invention, the N-terminal propeptide may be replaced or adapted to facilitate secretion or other handling or processing in the expression system.

The molecule may comprises a first moiety having the activity of the proα1(III) C-propeptide attached to a second moiety comprising the collagen α-chain and N-propeptide of the proα2(I) chain. The molecule may have the sequence of SEQ ID NO: 4.

In the natural formation of a collagen molecule in vivo, the N- and C-propeptides are cleaved off the procollagen molecule to yield a collagen molecule during the formation of polymeric collagen. Consequently, the invention includes within its scope a collagen molecule comprising a non-natural combination of α-chains. Non-natural collagen homotrimers and heterotrimers, including all the possible collagen trimers not mentioned in Table 1, are within the scope of the invention. (If for any reason it is desired to have a non-natural collagen molecule with a C-propeptide but not an N-propeptide, or vice versa, the enzymes responsible for processing in the chosen expression system may be manipulated or selected accordingly or the sequence of the molecule modified to make it susceptible to enzymatic processing as appropriate.)

Collagen molecules naturally self-assemble into collagen fibrils, which in turn aggregate to form a collagen fibre. Collagen fibrils and collagen fibres comprising collagen molecules as described above are therefore also contemplated by the invention.

Molecules of the first aspect of the invention may be prepared by any convenient method, including peptide ligation and complete synthesis. It is preferred however, that the molecules be prepared by expression from a recombinant DNA system. For this purpose, and according to a second aspect of the invention, there is provided a DNA molecule, which may be in recombinant or isolated form, encoding a molecule as described above (particularly a non-natural procollagen α-chain).

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and. preferably, to enable selection of cells harbouring vectors incorporating heterologous DNA. Appropriate start and stop signals may be present. The vector may be an expression vector having regulatory sequences to drive expression. Vectors not including regulatory sequences are useful as cloning vectors; and, of course, expression vectors may also be useful as cloning vectors.

Cloning vectors can be introduced into *E. coli* or another suitable host which facilitate their manipulation. According to another aspect of the invention, there is therefore provided a host cell transfected or transformed with DNA as described above. Such host cells may be prokaryotic or eukaryotic. Eukaryotic hosts may include yeasts, insect and mammalian cell lines. Expression hosts may be stably transformed. Unstable and cell-free expression systems may be used in appropriate circumstances, but it is unlikely that they will be favoured, at the present state of technology, for bulk production.

DNA of the invention may also be in the form of a transgene construct designed for expression in a transgenic plant or, preferably, animal. In principle, the invention is applicable to all animals, including birds such as domestic fowl, amphibian species and fish species. The protein may be harvested from body fluids or other body products (such as eggs, where appropriate). In practice, it will be to (non-human) mammals, particularly placental mammals, that the greatest commercially useful applicability is presently envisaged, as expression in the mammary gland, with subsequent optional recovery of the expression product from the milk, is a proven and preferred technology. It is with ungulates, particularly economically important ungulates such as cattle, sheep, goats, water buffalo, camels and pigs that the invention is likely to be most useful. The generation and usefulness of such mammalian transgenic mammary expression systems is both generally, and in certain instances specifically, disclosed in WO-A-8800239 and WO-9005188. The β-lactoglobulin promoter is especially preferred for use in transgenic mammary expression systems. WO-A-9416570 purports to disclose the production of human recombinant collagen in the milk of transgenic animals but contains no experimental details of such production having taken place.

Expression hosts, particularly transgenic animals, may contain other exogenous DNA to facilitate the expression, assembly, secretion and other aspects of the biosynthesis of molecules of the invention. For example, expression hosts may co-express prolyl 4-hydroxylase, which is a post-translational enzyme important in the natural biosynthesis of procollagens, as disclosed in WO-9307889.

DNA, particularly cDNA, encoding natural procollagen chains is known and available in the art. For example, WO-A-9307889, WO-A-9416570 and the references cited in both of them give details. Such DNA forms a convenient starting point for DNA of the present invention, which may be prepared by recombinant techniques from it. While in general terms DNA encoding a C-propeptide (or a minimal essential region from it) may simply be ligated to DNA encoding an alien collagen triple helical domain (usually attached to DNA encoding the corresponding N-propeptide), in practice it is useful to use PCR-based techniques to effect the precise ligation. For example, PCR products flanking the junction region between the C-propeptide and the triple helical domain may be prepared and combined; an overlap extension reaction can then be carried out to yield a PCR product which is a hybrid between DNA encoding the C-propeptide of one procollagen chain and DNA encoding the triple helical domain (and the N-propeptide, usually) of another procollagen chain.

The invention is in principle capable of accommodating the use of synthetic DNA sequences, cDNAs, full genomic sequences and "minigenes", which is to say partial genomic sequences containing some, but not all, of the introns present in the full length gene. Because of the large number of introns present in collagen genes in general, though, experimental practicalities will usually favour the use of cDNAs or, in some circumstances, minigenes.

DNA in accordance with the invention can in principle be prepared by any convenient method involving coupling together successive nucleotides, and/or ligating oligo- and/or poly-nucleotides, including in vitro processes, but recombinant DNA technology forms the method of choice.

Molecules of the invention may be useful in a method of treatment or diagnosis of the human or animal body. The invention therefore extends to molecules as described above for use in medicine.

The molecule may be for use as an adhesive or implant. It may be for use in promoting the healing of wounds or fibrotic disorders with reduced scarring. It may be for use in promoting the healing of chronic wounds. By "wounds or fibrotic disorders" is meant any condition which may result in the formation of scar tissue. In particular, this includes the healing of skin wounds, the repair of tendon damage, the healing of crush injuries, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis, cirrhosis of the liver, and proliferative vitreoretinopathy.

For example in the inhibition of fibrosis a novel collagen molecule or proαchain may be applied to a site of wounding or fibrosis, the novel collagen (or proα chain) inhibiting collagen fibril formation and thus fibrosis. The novel collagen or proα chain may for example have a shortened α-chain.

DNA of the invention may be useful, in appropriate constructs, in a method of gene therapy. It may be for use in the treatment of Osteogenesis Imperfecta (OI), Ehlers-Danlos Syndrome (EDS), Stickler Syndrome, Spondyloepiphyseal dysplasia, Hypochondrogenesis or Aortic Aneunrsms. Mutations within collagen genes are the cause of most forms of OI, some forms of EDS and of some chondrodysplasias. In most cases the devastating effects of the disease are due to substitutions of glycine within the triple helical domain—the Gly-X-Y repeat containing regionαfor amino acids with bulkier side chains.

This results in triple helix folding being prevented or delayed with the consequence that there is a drastic reduction in the secretion of trimerised proα chains. The malfolded proteins may be retained within the cell, probably within the ER (endoplasmic reticulum), where they are degraded. As the folding of the C-propeptide is not affected by these mutations within the triple helical domain. C-propeptides from wild-type as well as mutant chains associate and may be retained within the cell. The retention and degradation of wild-type chains due to their interaction with mutant chains amplifies the effect of the mutation and has been termed "procollagen suicide". The massive loss of protein due to this phenomenon may explain the dominant lethal effects of such mutations. By engineering proα chains having altered chain selectivity, proα chains maybe produced which do not associate with the mutant chains, and will therefore fold and be secreted normally. Such engineered proα chains may contain the wild-type collagen α-chain, thereby making up for the deficit caused by the mutant collagen α-chain. Expressed protein may in some circumstances also be useful in the treatment of diseases and conditions which could be addressed at a more fundamental level by gene therapy.

The invention may also be useful in photography, brewing, foodstuffs, textiles or adhesives.

Also provided according to the present invention is a method of treatment or diagnosis of the human or animal body comprising the use of a molecule according to the present invention.

BRIEF DESCRIPTION OF FIGURES

The invention will be further apparent from the examples, which comprise the following Figures and description of experiments, of which:

FIG. 2 shows an alignment plot made using the PILE-UP program on SEQNET at the Daresbury Laboratories, ULK using default settings, of the C-propeptides of proα chains of type I and type III procollagen. Alpha 1(I) is SEQ ID NO: 14; alpha 2(I) is residues number 284–534 of SEQ ID NO: 1; and alpha 1(III) is residues number 379–626 of SEQ ID NO: 2. C-proteinase cleavage sites (marked CP) are between A and D (alpha 1(I)), A and D (alpha 2(I)) and G and D (alpha 1(III)). Junction points A, F, B, C and G are as shown. Numbers indicate conserved cysteine residues. # indicates identical amino acids and~indicates amino acids with conserved side chains;

FIG. 3 shows recognition sequences for proα1(I), proα2 (I), proα1(II), proα1(III), proα1(V), proα2(V), proα1(XI) and proα2(XI) proα chains having SEQ ID NOs: 7, 8, 9, 6, 10, 11, 12, and 13 respectively and which were identified by alignment plots of C-propeptides against other C-propeptides (specifically, those of FIG. 2) as corresponding to the sequences in the regions between junction points B and G of FIG. 2;

EXPERIMENTAL

Figure 1:
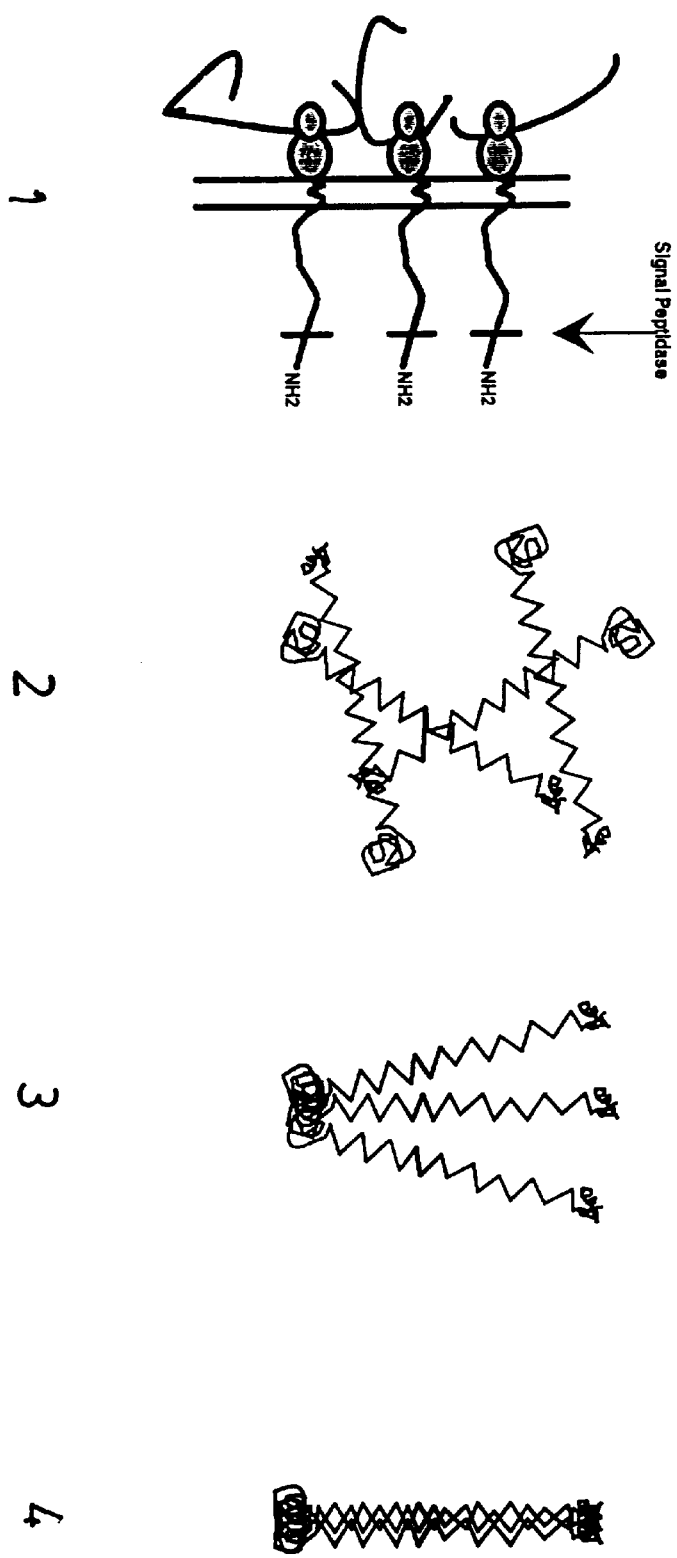
FIG. 1 shows the initial stages in the intra-cellular folding, assembly and modification of procollagen. As can be seen, co-translational translocation and signal peptide cleavage occurs at stage number 1. Intra-molecular disulphide bond formation then takes place as well as N-linked glycosylation, proline isomerisation and proline hydroxylation at stage 2. There then follows at stage 3 type-specific assembly of the proα chains by trimerisation and intermolecular disulphide bond formation. Finally, at stage 4, triple helix formation proceeds in a carboxy-to-amino-direction to give trimerised proαchains.

A cDNA clone coding for a truncated proα2(I) chain (designated proα2(I)Δ1; SEQ ID NO: 1; nucleic acid coding sequence—SEQ ID NO: 19) was constructed from two partial cDNA clones, pHf1131 and pHp2010 (Kuivaniemi, H. et al., 1988, Biochem. J., 252: 633–640) which were sub-cloned into the EcoRI site of pBluescript SK$^+$. A 3.4 kb fragment PstI fragment containing the vector and the 5'-terminal 0.5 kb of the gene was isolated from pHp2010 and ligated to a 1.4 kb PstI fragment derived from pHf1131 encoding the 3' terminus. The resultant recombinant, proα2 (I)Δ1, has a 2.2 kb deletion in the coding sequence (Lees and Bulleid, 1994, J. Biol. Chem., 269: 24354–24360).

This construct was analysed using a semi-permeabilised (SP) HT1080 cell system as described by Wilson et al.

(1995, Biochem J. 307: 679–687). Semi-permeabilised cells were prepared from HT1080 cells. Confluent HT1080 cells from a 75 cm² flask were rinsed once with PBS (phosphate buffered saline), then incubated with 2 ml of PBS containing 2.5 mg/ml trypsin for 3 minutes at room temperature. The flask was transferred to ice where 8 ml of ice-cold KHM (110 mM KOAc. 20 mM Hepes, pH 7.2, 2 mM MgOAc) was added containing 100 μg/ml soyabean trypsin inhibitor and the cells released from the plate. Cells were pelleted at 12,000 rpm for 3 minutes and resuspended in 6 ml of KHM containing 40 μg/ml digitonin (diluted from a 40 mg/ml stock in DMSO (dimethyl sulfoxide)) and incubated on ice for 5 minutes. To terminate permeabilisation 8 ml of KHM was added and cells were pelleted and resuspended in 50 mM Hepes, pH 7.2, 90 mM KOAc. After 10 minutes the cells were pelleted and resuspended in 100 μl of KHM (approximately 2×10⁶ cells). Endogenous mRNA was removed by adding $CaCl_2$ to 1 mM and Staphylococcal nuclease to 10 μg/ml and incubating at room temperature for 12 minutes. The reaction was terminated by the addition of EGTA to 4 mM, and pelleting the cells. Semi-permeabilised cells were resuspended in 100 μl of KHM. RNA was translated using a rabbit reticulocyte lysate (FlexiLysate, Promega, Southampton, U.K.) for 1 hour at 30° C. The translation reaction (25 μl) contained 16 μl reticulocyte lysate, 1 μl 1 mM amino acids (minus methionine), 15 μCi L-[³⁵S] methionine, 1 μl transcribed RNA and semi-permeabilised cells (approx. 1×10⁵). After translation, N-ethylmaleimide was added to a final concentration of 20 mM. The formation of disuiphide bonds was verified by comparative gel electrophoresis on 7.5% polyacrylamide gel of translation products run under reducing and non-reducing conditions.

Figure 4:
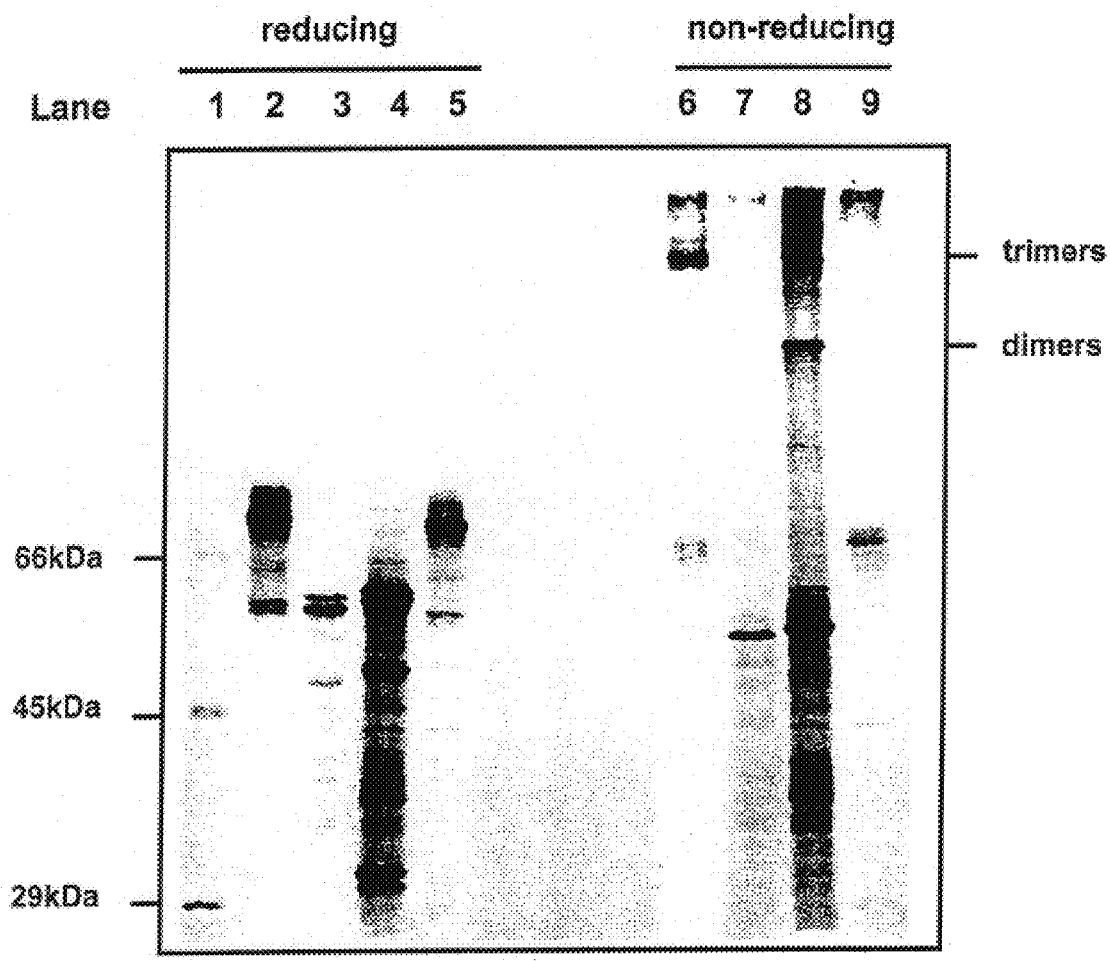
FIG. 4 shows an SDS-PAGE gel of translated procoliagen constructs. Lanes are as follows: 1—molecular weight markers; 2 and 6—proα1(III)Δ1; 3 and 7—proα2(I)Δ1; 4 and 8—proα2(I):(III)CP; 5 and 9—proα (III):(I)CP.

When analysed using this cell-free system the translation product from proα2(I)Δ1 mRNA did not self-associate to form homotrimers indicating that it does not contain the information necessary for the initial recognition event (FIG. 4, lanes 3 and 7).

A cDNA clone coding for a truncated proα1(III) chain (designated proα1(III)Δ1; SEQ ID NO: 2; nucleic acid coding sequence—SEQ ID NO: 20) was constructed from a full-length type III procollagen cDNA which was constructed from two partial cDNAs, pS413 and pS31 (Ala-Kokko, et al., 1989, Biochem. J., 260: 509–516). Each cDNA was subcloned into the EcoRI site of pBluescript SK⁻. A 4.7 kb Sal I (restriction enzyme) fragment containing the vector and the 5' terminal 1.8 kb was isolated from pS413 and ligated to a 3.6 kb Sal I fragment derived from pS31 to produce proα1(III). An internal 2.5 kb XhoI fragment was excised from proα1(III) and the parental plasmid re-ligated to create proα1(III)Δ1 (Lees and Bulleid, 1994, J. Biol. Chem., 269: 24354–24360).

The translation product from proα1(III)Δ1 mRNA was able to assemble to form a homotrimer as judged by its ability to form inter-chain disulphide bonded dimers and trimers when translated in a semi-permeabilised cell-free translation system. This demonstrated that it contained the information required for self-assembly (FIG. 4, lanes 2 and 6).

Hybrid cDNA clones were prepared which contained sequences derived from proα1(III)Δ1 and proα2(I)Δ1. The C-proteinase cleavage site of proα1(III)Δ1 was, for these experiments, taken to be between Ala 377 and Pro 378 of SEQ ID NO: 2, instead of between Gly 381 and Asp 382 of SEQ ID NO: 2 as shown in FIG. 2. In the first of these constructs the coding sequence for the C-propeptide from the proα1(III)Δ1 chain was replaced by that for the C-propeptide from the proα2(I) chain, the resulting chimera being designated proα1(III):(I)CP (SEQ ID NO: 3). This construct failed to self-associate when translated in the cell-free system (FIG. 4, lanes 5 and 9). A reciprocal construct was made where the C-propeptide from the proα2 (I)Δ1 was replaced with the C-propeptide from the proα1 (III) chain with the resulting chimera designated proα2(I): (III)CP (SEQ ID NO: 4).

This construct was able to self associate to form dimers and homotrimers (FIG. 4, lanes 4 and 8), demonstrating directly for the first time that all the information required for selective association resides within the C-propeptide. The construct proα1(III):(I)CP was prepared as described below. Other constructs were produced using the same approach and published sequences.

The hybrid cDNA clones were prepared using a PCR-based approach. For the construction of proα1(III):(I)CP, a PCR product was prepared from proα1(III)Δ1 with primers, one of which (SEQ ID NO: 15; JL-35) hybridised within the triple helical domain whilst the other (SEQ ID NO: 16; JL-32) hybridised with 21 nucleotides upstream from the junction point at the C-propeptide. This primer also contained an overlap of 21 nucleotides which were complimentary to the first 21 nucleotides of the C-propeptide of proα2(I)Δ1. This gave a 0.25 Kb PCR product.

A second PCR product was prepared from proα2(I)Δ1 with primers, one of which (SEQ ID NO: 17; JL-3IKpn) hybridised downstream from the stop codon for translation within the 3'-non-translated region. This primer also contained a KpnI site. The other primer (SEQ ID NO: 18; JL-36) hybridised with the first 18 nucleotides of the C-propeptide of proα2(I)Δ1. This gave a 0.85 Kb PCR product.

The two PCR products were combined and a third PCR (an overlap extension) was carried out with primers JL-35 (SEQ ID NO: 15) and JL-31Kpn (SEQ ID NO: 17) to yield a 1.1 Kb product. This was cut with XhoI and KpnI and subcloned into XhoI and KpnI cut proα1(III)Δ1 to yield proα1(III):(I)CP.

A variety of hybrid constructs were then prepared in which parts of the proα2(I)Δ1 C-propeptide sequence was replaced with the corresponding region from the proα1(III) C-propeptide. The various regions are outlined in FIG. 2 with the junction points designated as A, F, B, C, and G. So for example the A-join molecule contains all of the proα2 (I)Δ1 sequence up to but not including the A site (i.e. . . . DY) with all of the sequence carboxy-to this site (i.e. ET . . . ) being derived from the corresponding region from the C-propeptide of the proα1(III) chain. Pros 1(III) and proα2 (I) C-propeptides differ in their complement of cysteine residues (and hence in their ability to form disulphide bonds), with proα2(I) lacking the Cys 2 residue (FIG. 2), instead having a serine residue. In order to ease analysis under non-reducing conditions (see below) the F, B and C constructs contained a serine to cysteine mutation at the Cys 2 site of the proα2(I) chain. To ensure that this mutation played no role in chain selection, a similarly mutated construct (proα2(I):(III) BGR$^{S-C}$; also referred to as BGR$^{S-C}$; see below) was back-mutated. The back-mutated construct (i.e. proα2(I):(III) BGR$^{S-C}$—also referred to as BGR) had the same chain selectivity as its parent molecule (proα2(I): (III) BGR$^{S-C}$) (see below).

Figure 5:
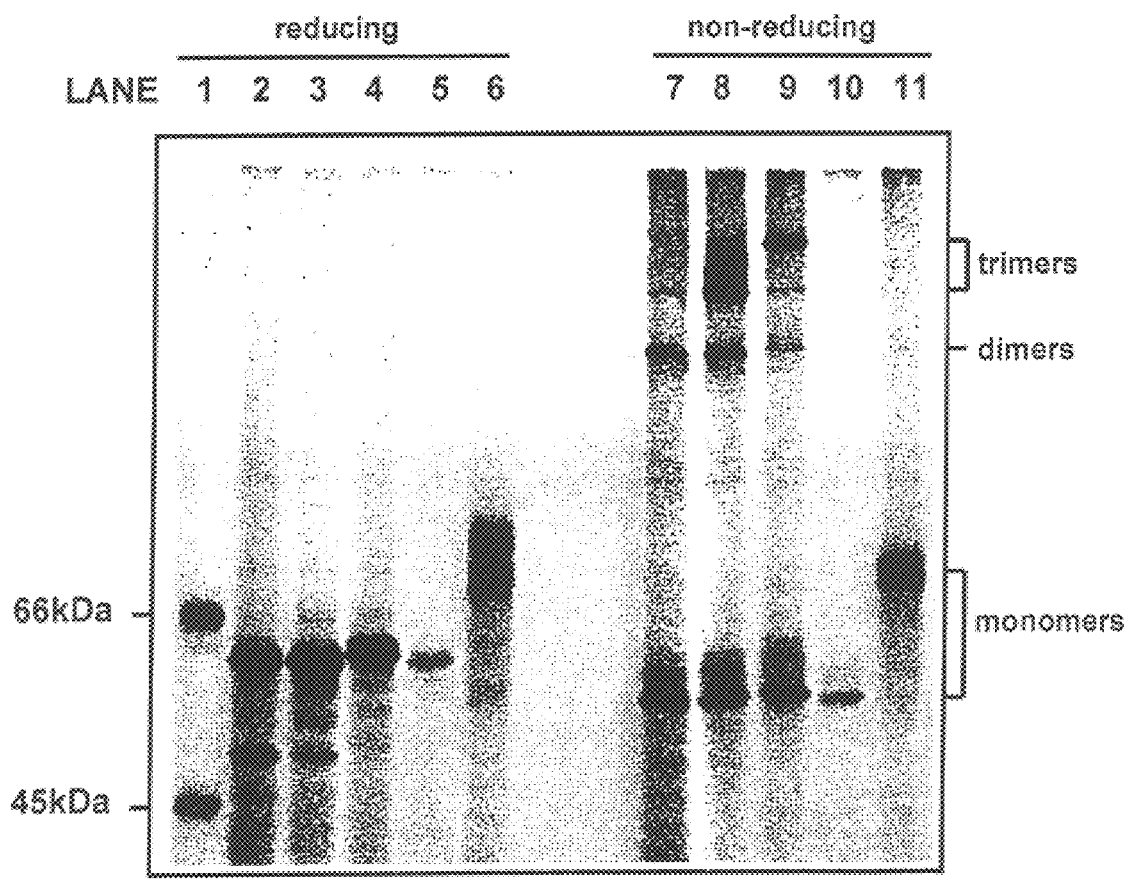
FIG. 5 shows an SDS-PAGE gel of translated procollagen constructs. Lanes are as follows: 1—molecular weight markers; 2 and 7—A-join; 3 and 8—F-join; 4 and 9—B-join; 5 and 10—C-join; 6 and 11—recip-C-join.

The A-join, F-join and B-join chimeras all assembled to form homotrimers when translated in the cell-free system (FIG. 5, lanes 7, 8 and 9). However, the C-join molecule did not assemble (FIG. 5, lane 10) suggesting that the recognition site for assembly was contained within the sequence carboxy-terminal to the B-site and amino-terminal to the C-site. The possibility that the lack of assembly of the C-join molecule was due to this site being within the recognition sequence for assembly could not be ruled out. Evidence that the recognition site had been disrupted was obtained when the reciprocal construct was made. This construct contained the proα1(III)Δ1 chain up to the C-site with the rest of the C-propeptide being derived from the proα2(I) C-propeptide. No assembly occurred from this construct (recip-C-join) illustrating that the recognition site had been disrupted (FIG. 5, lane 11).

Figure 7:
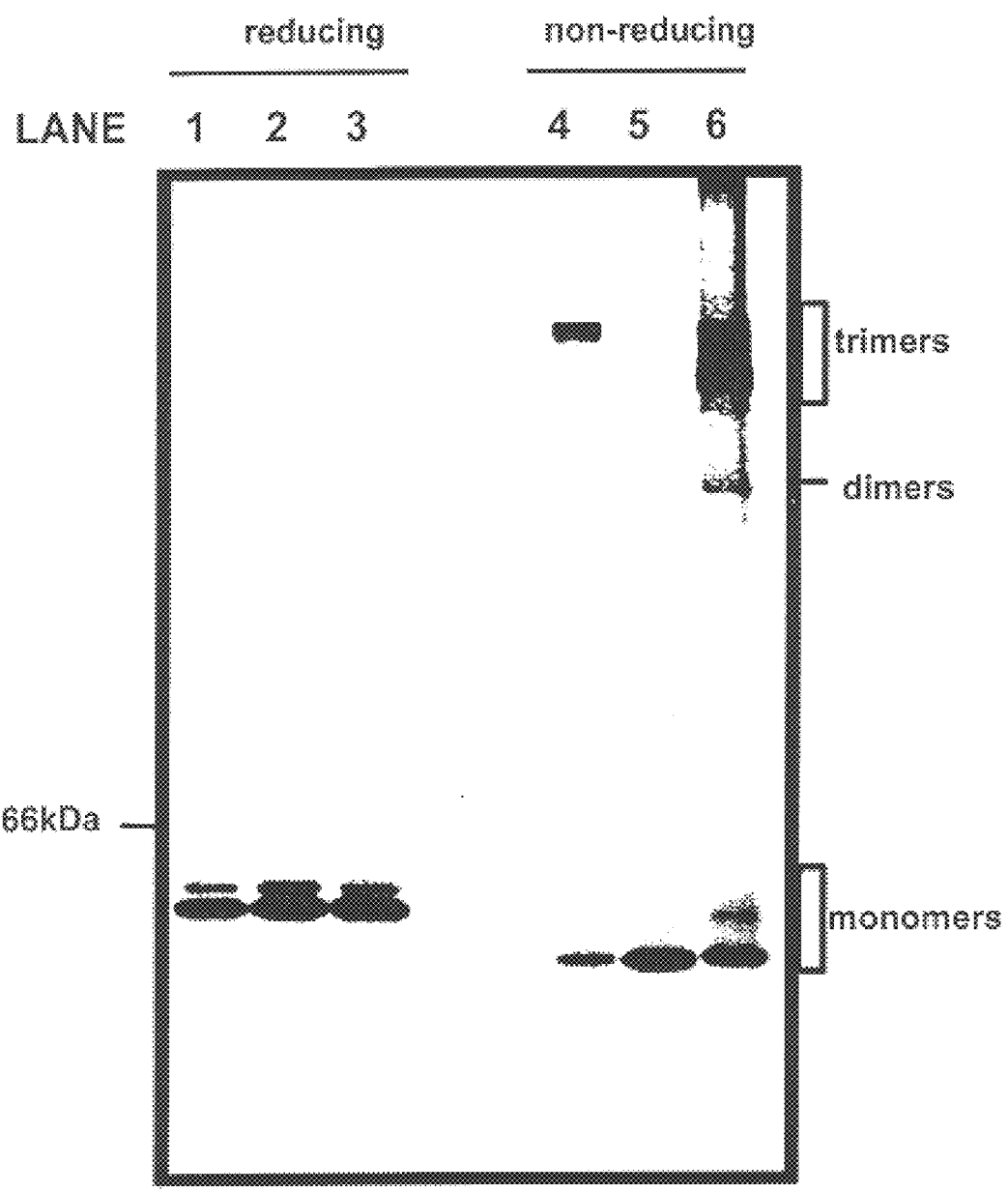
FIG. 7 shows an SDS-PAGE gel of translated procollagen constructs under reducing (lanes 1–3) and non-reducing (lanes 4–6) conditions. Lanes are as follows: 1 and 4—BGR$^{S-C}$; 2 and 5—BGR; 3 and 6—BGR$^{L-M}$.

The next construct made contained all of the proα2(I)Δ1 sequence apart from a short stretch of 23 amino acids between the B-site and the G-site (SEQ ID NO: 6) which were replaced with the corresponding region from the C-propeptide of proα1(III). This construct (designated BGR; SEQ ID NO: 5) was altered by site directed mutagenesis of cysteine for serine at the Cys 2 site of the proα2(I) part of the molecule (i.e. cysteine was substituted for the serine 335 residue of SEQ ID NO: 5). The resultant molecule (designated proα2(I):(III) BGR$^{S\text{-}C}$ was shown to assemble to form inter-chain disulphide bonded homotrimers when translated in the cell-free system (FIG. 7, lane 4), demonstrating that this short stretch of 23 amino acids contains all the information to drive homotrimer formation.

To verify that the serine to cysteine mutation did not affect chain selection, a back mutation was made (i.e. to give proα2(I):(III) BGR) and homotrimer formation analysed. As expected, no inter-chain disulphide bonded trimers were detected (FIG. 7, lane 5) as this molecule does not contain the cysteine residue required for inter-chain disulphide bond formation.

Figure 6:
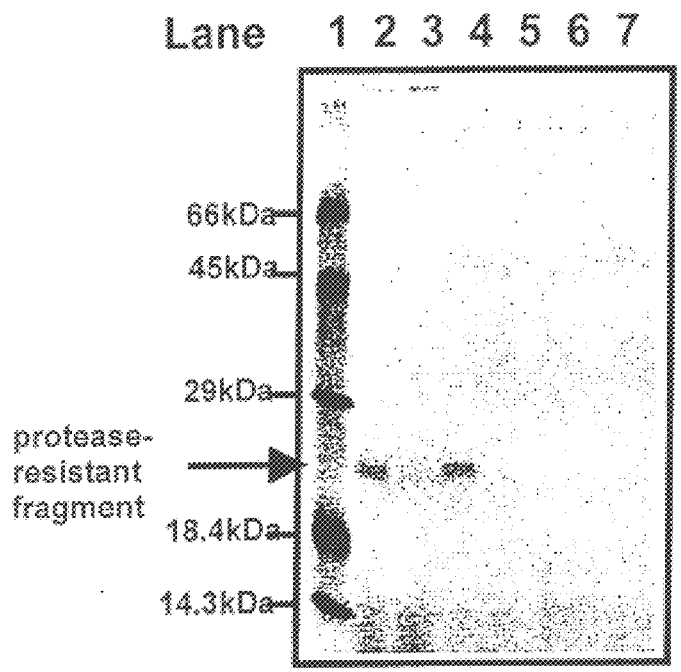
FIG. 6 shows translated procollagens in the presence (Lanes 3, 5 and 7) and absence (Lanes 2, 4 and 6) of α,α'-dipyridyl. Lanes are as follows: 2 and 3—proα2(I): (III)CP; 4 and 5—BGR; 6 and 7—proα1(III):(I)CP.
Figure 8:
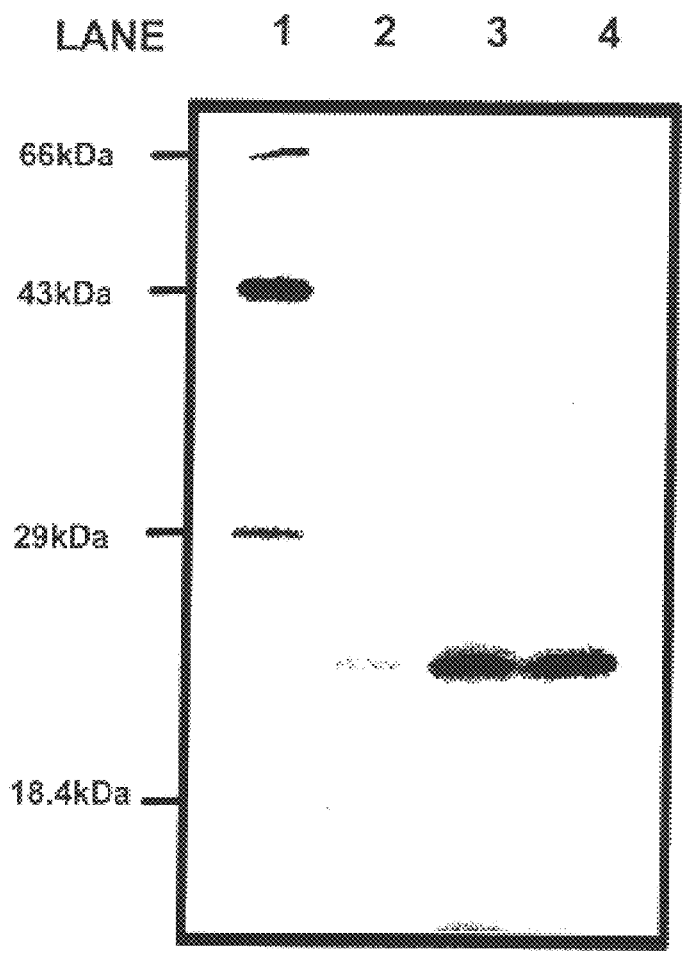
FIG. 8 shows an SDS-PAGE gel of translated procollagen constructs. Lanes are as follows: 1—molecular weight markers; 2—BGR$^{S-C}$; 3—BGR; 4—BGR$^{L-M}$.

To determine whether a stable triple helix was formed after translation of the chimeric procollagens, a simple protease protection assay was carried out. This involved treating the translation products with a combination of proteolytic enzymes (trypsin, chymotrypsin and pepsin). Isolated SP-cells following translation were resuspended in 0.5 M acetic acid in 1% (v/v) Triton X-100 and incubated with pepsin (100 mg/ml) for 2 hours at 20° C. Digestions were stopped by neutralisation with 1 M Tris base and proteins precipitated with ethanol at a final concentration of 27% (v/v). Precipitated protein from pepsin digests were resuspended in 50 mM Tris-HCl, pH 7.4 containing 0.15 M NaCl, 10 mM EDTA (ethylenediaminetetra-acetic acid) and 1% Triton X-100. Chymotrypsin and trypsin were added to a final concentration of 250 µg/ml and 100 µg/ml respectively and samples incubated at room temperature for 2 minutes. The digestion was stopped by the addition of soyabean trypsin inhibitor to a final concentration of 500 µg/ml and 5 volumes of boiling SDS-PAGE (sodium dodecyl sulphate-polyacrylamide gel electrophoresis) sample buffer and boiling the samples for 3 minutes. The results are shown in FIGS. 6 and 8. The formation of a stable triple helix is characterised by the appearance of a protease resistant fragment (corresponding to the triple helical domain) after digestion. Only the products of translation of the proα2(I):(III)CP (FIG. 6, lane 2) and the BGR constructs (FIG. 6, lane 4; FIG. 8, lanes 2 and 3) generated a protease resistant fragment which were only formed when α,α'-dipyridyl (an inhibitor of prolyl 4-hydroxylase) was not present during the translation (FIG. 6). As proline hydroxylation is necessary for formation of a thermally stable triple helix, this demonstrates that a correctly folded triple helix was formed with these constructs.

This also demonstrates that although BGR was not able to form trimers stabilised by inter-chain disulphide bonds, it was able to trimerise to form a correctly aligned triple helix.

Analysis of the B-G motif from the proα1(III) and proα2 (I) chains (FIG. 3) shows that of the residues in the recognition sequences (FIG. 3; SEQ ID NOs: 6 and 8 respectively), residues 13–20 are identical with the exception of residue 17—Leu (L) in proα1(III) and Met (M) in proα2(I). In order to determine the role played by these residues in the chain selection process, site directed mutagenesis was used to substitute Met for Leu in the proα1(III) recognition sequence in the proα2(I):(III) BGR$^{S\text{-}C}$ construct (designated proα2(I):(III) BGR$^{L\text{-}M}$—also referred to as BGR$^{L\text{-}M}$), i.e. residue Leu 425 of SEQ ID NO: 5 was substituted for Met, and residue Ser 335 was substituted for Cys.

Chain assembly of proα2(I):(III) BGR$^{L\text{-}M}$ was performed as described above and the electrophoretic mobility of the chains analysed. Under non-reducing conditions this construct formed inter-chain disulphide bonds (FIG. 7, lane 6), and formed protease-resistant triple helical domains (FIG. 8, lane 4). The substitution of Leu for Met did not, therefore, disrupt the process of chain selection nor did it prevent the formation of a correctly aligned helix.

TABLE 1

| Type | Chains | Molecules | Distribution |
| --- | --- | --- | --- |
| I | α1(I) | major [α1(I)]$_2$α2(I) | widespread, skin, |
|  | α2(I) | minor [α1(I)]$_3$ | bone, tendon, ligament, cornea. |
| II | α1(II) | homotrimers [α1(II)]$_3$ | cartilage, notochord, invertebrate disc, ear, developing bone, eye, cornea |
| III | α1(III) | homotrimers [α1(III)$_3$] | widespread, particularly found with type I collagen |
| V | α1(V) | heterotrimers | widespread, |
|  | α2(V) |  | particularly found in |
|  | α3(V) |  | cornea with type I collagen |
| XI | α1(XI) | heterotrimers | cartilage, cornea |
|  | α2(XI) |  | and vitreous |
|  | α3(XI) |  |  |
|  | α3(XI) = α1(II) |  |  |

What is claimed is:

1. A polypeptide comprising:
   i) a first moiety having activity for assembly into a trimeric procollagen C-propeptide and being from a first type of pro-α chain, wherein said first moiety contains a recognition sequence for chain selection, and;
   ii) a second moiety containing a triple helix forming domain from a pro-α chain different from said first type,
       said first moiety being attached to said second moiety so that said recognition sequence permits co-assembly of said polypeptide with other polypeptides having said activity and a triple helix forming domain.

2. The polypeptide according to claim 1 wherein said recognition sequence is selected from the group consisting of the proα1(I), proα2(I), proα1(II), proα1(III), proα1(V), proα2(V), proα3(V), proα1(XI), proα2(XI) and proα3(XI) chain recognition sequences.

3. The polypeptide according to claim 1 wherein the recognition sequence is selected from the group consisting of the sequence of SEQ ID NO:6, SEQ ID NO:7, SEQ ID NO:8, SEQ ID NO:9, SEQ ID NO:10, SEQ ID NO:11, SEQ ID NO:12 and SEQ ID NO:13.

4. The polypeptide according to claim 1 wherein the recognition sequence is that of a fibrillar proα chain.

5. The polypeptide according to claim 1 wherein the second moiety comprises at least a collagen α-chain.

6. The polypeptide according to claim 5 wherein the collagen α-chain is selected from the group consisting of proα1(I), proα2(I), proα1(II), proα1(III), proα1(V), proα2(V), proα3(V), proα1(XI), proα2(XI) and proα3(XI) chain collagen α-chains.

7. The polypeptide according to claim 1 wherein the second moiety further comprises a proα chain N-propeptide.

8. The polypeptide according to claim 7 wherein the N-propeptide is selected from the group consisting of the proα1(I), proα2(I), proα1(II), proα1(III), proα1(V), proα2(V), proα3(V), proα1(XI), proα2(XI) and proα3(XI) chain N-propeptides.

9. The polypeptide according to claim 8 wherein said first moiety contains the proα1(III) C-propeptide recognition sequence and the second moiety contains the triple helix forming domain and N-propeptide from the proα2(I) chain.

10. The polypeptide according to claim 7 wherein said polypeptide has the sequence of SEQ ID NO:4.

11. The polypeptide according to claim 1 wherein said first and second moieties are separated by intervening amino acid residues.

12. A method of preparing a procollagen molecule comprising co-assembling the polypeptide as claimed in claim 1 with two further polypeptides each having said activity and triple helical forming domain, whereby said polypeptide according to claim 1 and said further polypeptides co-assemble to produce a molecule having a triple helical domain.

13. A method of producing a collagen comprising preparing a procollagen and converting said procollagen to said collagen,
   said procollagen being prepared by a method comprising co-assembling a first polypeptide with two further polypeptides each of said polypeptides having activity for assembly into a trimeric procollagen C-propeptide and a triple helical forming domain, said first polypeptide comprising:
   i) a first moiety having activity for assembly into a trimeric procollagen C-propeptide and being from a first type of pro-α chain, wherein said first moiety contains a recognition sequence for chain selection, and
   ii) a second moiety containing a triple helix forming domain,
   said first moiety being attached to said second moiety so that said recognition sequence permits co-assembly of said first polypeptide with said two further polypeptides molecules having said activity and a triple helix forming domain, whereby said first polypeptide and said two further polypeptides co-assemble to produce a molecule having a triple helical domain.

14. A collogen molecule produced by the method of claim 13.

15. A collagen fibril comprising collagen molecules according to claim 14.

16. A collagen fibre comprising collagen fibrils according to claim 15.

17. A DNA molecule encoding the polypeptide according to claim 1.

18. An expression host cell transformed or transfected with the DNA molecule according to claim 17 operably linked to a regulatory sequence that directs expression.

19. A method of producing a collagen, the method comprising culturing the host cell according to claim 18 under conditions such that collagen is produced, harvesting said collagen from said expression host cell and optionally subsequently purifying said collagen.

* * * * *